(12) United States Patent
Belkin et al.

(10) Patent No.: US 10,702,416 B2
(45) Date of Patent: Jul. 7, 2020

(54) SYSTEM FOR GLAUCOMA TREATMENT

(71) Applicant: BELKIN LASER LTD., Tel Aviv (IL)

(72) Inventors: Michael Belkin, Givat Shmu'el (IL); David Zigdon, Tel Aviv (IL); Ziv Karni, Caesarea (IL); Asaf Klein, Caesarea (IL)

(73) Assignee: BELKIN LASER LTD., Yavne (IL)

( * ) Notice: Subject to any disclaimer, the term of this patent is extended or adjusted under 35 U.S.C. 154(b) by 488 days.

(21) Appl. No.: 14/765,862

(22) PCT Filed: Feb. 13, 2014

(86) PCT No.: PCT/IB2014/058973
§ 371 (c)(1),
(2) Date: Aug. 5, 2015

(87) PCT Pub. No.: WO2014/132162
PCT Pub. Date: Sep. 4, 2014

(65) Prior Publication Data
US 2015/0366706 A1 Dec. 24, 2015

Related U.S. Application Data

(60) Provisional application No. 61/769,282, filed on Feb. 26, 2013.

(51) Int. Cl.
*A61F 9/008* (2006.01)
*A61F 9/007* (2006.01)

(52) U.S. Cl.
CPC .......... *A61F 9/008* (2013.01); *A61F 9/00781* (2013.01); *A61F 2009/00868* (2013.01); *A61F 2009/00891* (2013.01)

(58) Field of Classification Search
CPC .................. A61F 9/008; A61F 9/00781; A61F 2009/00868; A61F 2009/00891
See application file for complete search history.

(56) References Cited

U.S. PATENT DOCUMENTS

| 2,635,502 A | 4/1953 | Richards |
| 3,594,072 A | 7/1971 | Feather et al. |
| 4,641,349 A | 2/1987 | Flom et al. |

(Continued)

FOREIGN PATENT DOCUMENTS

| CN | 201537172 U | 8/2010 |
| DE | 202016006265 U1 | 3/2017 |

(Continued)

OTHER PUBLICATIONS

U.S. Appl. No. 13/669,961 Office Action dated Dec. 15, 2015.
(Continued)

*Primary Examiner* — Boniface N Nganga
(74) *Attorney, Agent, or Firm* — Kligler & Associates Patent Attorneys Ltd

(57) ABSTRACT

An apparatus (20) includes a probe (36) and a processor (144). The probe is positioned adjacent to an eye (28) of a patient (32) and is configured to irradiate a trabecular meshwork (56) of the eye with one or more optical beams (52). The processor is configured to select one or more target regions (80) of the trabecular meshwork, and to control the probe to irradiate the selected target regions with the optical beams.

34 Claims, 3 Drawing Sheets

(56) References Cited

U.S. PATENT DOCUMENTS

| | | | |
|---|---|---|---|
| 4,718,418 A | 1/1988 | L'Esperance | |
| 4,966,452 A | 10/1990 | Shields et al. | |
| 5,123,902 A | 6/1992 | Muller et al. | |
| 5,152,760 A | 10/1992 | Latina | |
| 5,370,641 A | 12/1994 | O'Donnell, Jr. | |
| 5,479,222 A | 12/1995 | Volk et al. | |
| 5,549,596 A | 8/1996 | Latina | |
| 5,598,007 A | 1/1997 | Bunce et al. | |
| 5,786,883 A | 7/1998 | Miller et al. | |
| 5,865,830 A | 2/1999 | Parel et al. | |
| 6,027,216 A | 2/2000 | Guyton et al. | |
| 6,033,396 A | 3/2000 | Huang et al. | |
| 6,059,772 A | 5/2000 | Hsia et al. | |
| 6,096,029 A | 8/2000 | O'Donnell, Jr. | |
| 6,099,521 A | 8/2000 | Shadduck | |
| 6,099,522 A * | 8/2000 | Knopp | B23K 26/04 606/10 |
| 6,146,375 A | 11/2000 | Juhasz et al. | |
| 6,210,399 B1 | 4/2001 | Parel et al. | |
| 6,258,082 B1 | 7/2001 | Lin | |
| 6,263,879 B1 | 7/2001 | Lin | |
| 6,319,274 B1 | 11/2001 | Shadduck | |
| 6,325,792 B1 * | 12/2001 | Swinger | A61F 9/00804 606/11 |
| 6,454,763 B1 | 9/2002 | Motter et al. | |
| 6,514,241 B1 | 2/2003 | Hsia et al. | |
| 6,530,916 B1 | 3/2003 | Shimmick | |
| 6,616,275 B1 | 9/2003 | Dick et al. | |
| 6,673,062 B2 | 1/2004 | Yee et al. | |
| 6,685,317 B2 | 2/2004 | Su et al. | |
| 6,698,886 B2 | 3/2004 | Pollack et al. | |
| 6,736,806 B2 | 5/2004 | Ruiz et al. | |
| 6,979,328 B2 | 12/2005 | Baerveldt et al. | |
| 7,252,661 B2 | 8/2007 | Nguyen et al. | |
| 7,282,046 B2 | 10/2007 | Simon | |
| 7,792,249 B2 | 9/2010 | Gertner et al. | |
| 8,004,764 B2 | 8/2011 | Artsyukhovich et al. | |
| 8,048,065 B2 | 11/2011 | Grecu et al. | |
| 8,109,635 B2 | 2/2012 | Allon et al. | |
| 8,442,185 B2 | 5/2013 | Gertner et al. | |
| 8,475,433 B2 | 7/2013 | Mrochen et al. | |
| 8,568,393 B2 | 10/2013 | Palanker | |
| 8,630,388 B2 | 1/2014 | Gertner et al. | |
| 8,679,100 B2 | 3/2014 | Raksi et al. | |
| 8,709,029 B2 | 4/2014 | Griffis, III et al. | |
| 8,771,261 B2 | 7/2014 | Andersen et al. | |
| 9,220,407 B2 | 12/2015 | Yam et al. | |
| 9,480,599 B2 | 1/2016 | Degani et al. | |
| 9,504,609 B2 | 11/2016 | Kurtz | |
| 9,622,911 B2 | 4/2017 | Rubinfeld et al. | |
| 9,840,599 B2 | 12/2017 | Koers et al. | |
| 9,849,034 B2 | 12/2017 | Artsyukhovich et al. | |
| 9,968,483 B2 | 5/2018 | Takeda et al. | |
| 2001/0027314 A1 | 10/2001 | Peyman | |
| 2005/0096639 A1 | 5/2005 | Slatkine et al. | |
| 2005/0107774 A1 | 5/2005 | Lin | |
| 2005/0254009 A1 | 11/2005 | Baker et al. | |
| 2005/0286019 A1 * | 12/2005 | Wiltberger | A61B 3/0091 351/211 |
| 2005/0288745 A1 | 12/2005 | Andersen et al. | |
| 2007/0081166 A1 * | 4/2007 | Brown | A61B 3/1005 356/479 |
| 2007/0129709 A1 | 6/2007 | Andersen et al. | |
| 2007/0159600 A1 | 7/2007 | Gil et al. | |
| 2007/0213693 A1 | 9/2007 | Plunkett | |
| 2008/0089481 A1 | 4/2008 | Gertner | |
| 2008/0108934 A1 | 5/2008 | Berlin et al. | |
| 2008/0161781 A1 | 7/2008 | McArdle et al. | |
| 2008/0204658 A1 * | 8/2008 | Van Saarloos | A61B 3/113 351/210 |
| 2009/0157062 A1 * | 6/2009 | Hauger | A61B 3/102 606/5 |
| 2010/0002837 A1 | 1/2010 | Gertner et al. | |
| 2010/0076419 A1 * | 3/2010 | Chew | A61F 9/008 606/6 |
| 2010/0324543 A1 | 12/2010 | Kurtz et al. | |
| 2011/0144627 A1 | 6/2011 | Smith | |
| 2011/0190741 A1 | 8/2011 | Deisinger et al. | |
| 2012/0083772 A1 | 4/2012 | Rubinfeld et al. | |
| 2012/0089134 A1 | 4/2012 | Horvath et al. | |
| 2012/0283557 A1 | 11/2012 | Berlin | |
| 2013/0103011 A1 * | 4/2013 | Grant | A61F 9/00825 606/4 |
| 2013/0123761 A1 | 5/2013 | Belkin et al. | |
| 2013/0204236 A1 * | 8/2013 | Awdeh | A61F 9/00802 606/4 |
| 2013/0218145 A1 | 8/2013 | Belkin et al. | |
| 2013/0289450 A1 | 10/2013 | Homer | |
| 2014/0094785 A1 | 4/2014 | Charles | |
| 2014/0135747 A1 * | 5/2014 | Donitzky | A61F 9/00827 606/4 |
| 2014/0135753 A1 | 5/2014 | Feklistov et al. | |
| 2014/0307077 A1 | 10/2014 | Prabhakar | |
| 2015/0223683 A1 | 8/2015 | Davidovics et al. | |
| 2015/0266706 A1 | 9/2015 | Hashimoto | |
| 2015/0313759 A1 | 11/2015 | Vera et al. | |
| 2016/0008172 A1 | 1/2016 | Kahook et al. | |
| 2016/0113816 A1 | 4/2016 | Herekar et al. | |
| 2016/0346126 A1 | 12/2016 | Luttrull et al. | |
| 2017/0038284 A1 | 2/2017 | Nemati | |
| 2017/0087014 A1 | 3/2017 | Potter, Jr. et al. | |
| 2017/0340483 A1 | 11/2017 | Rill et al. | |
| 2017/0360604 A1 | 12/2017 | Bach et al. | |
| 2018/0168737 A1 | 6/2018 | Ren et al. | |

FOREIGN PATENT DOCUMENTS

| | | | |
|---|---|---|---|
| EP | 0224322 | 6/1987 | |
| EP | 0224322 A1 | 6/1987 | |
| EP | 0651982 | 5/1995 | |
| EP | 0651982 A1 | 5/1995 | |
| EP | 2602005 A1 | 6/2013 | |
| FR | 2655837 A1 | 6/1991 | |
| JP | 2010148635 A | 7/2010 | |
| WO | 9216259 A1 | 10/1992 | |
| WO | 1998022016 A2 | 5/1998 | |
| WO | 2007103349 A2 | 9/2007 | |
| WO | 2008112236 A1 | 9/2008 | |
| WO | 2011085274 A1 | 7/2011 | |
| WO | WO 2011151812 A1 * | 12/2011 | A61F 9/008 |
| WO | WO-2013004255 A1 * | 1/2013 | A61F 9/00827 |
| WO | 2013059481 A1 | 4/2013 | |
| WO | 2018049246 A1 | 3/2018 | |

OTHER PUBLICATIONS

CN Application # 2014800101570 Office Action dated May 17, 2016.
U.S. Appl. No. 13/669,961 Office Action dated Jul. 26, 2016.
Smith et al., "Light scatter from the central human cornea", Journal "Eye", issue 4, pp. 584-588, year 1990.
European Application # 14757324.0 search report dated Oct. 11, 2016.
U.S. Appl. No. 13/669,961 Advisory Action dated Oct. 4, 2016.
Turati et al., "Patterned Laser Trabeculoplasty", Ophthalmic Surgery, Lasers and Imaging , vol. 41, No. 5, pp. 538-545, 2010.
Nozaki et al.,"Patterned Laser Trabeculoplasty with PASCAL streamline 577", Investigative Ophthalmology & Visual Science, vol. 54, p. 1867, Jun. 2013.
U.S. Appl. No. 13/669,961 Office Action dated Apr. 7, 2017.
EP Application # 11724805.4 office action dated Sep. 7, 2017.
JP Application # 2015-558576 office action dated Oct. 25, 2017.
U.S. Appl. No. 13/669,961 office action dated Nov. 17, 2017.
International Application PCT/IB2014/058973 Search Report dated Jun. 22, 2014.
U.S. Appl. No. 13/669,961 Office Action dated Apr. 8, 2013.
U.S. Appl. No. 13/669,961 Office Action dated May 7, 2014.
U.S. Appl. No. 13/669,961 Office Action dated Mar. 23, 2015.
U.S. Appl. No. 13/669,961 Office Action dated Jul. 22, 2015.

(56) References Cited

OTHER PUBLICATIONS

Barkana et al., "Selective Laser Trabeculoplasty", Survey of Ophthalmology, vol. 52, No. 6, pp. 634-653, year 2007.
Ivandic et al., "Early Diagnosis of Ocular Hypertension Using a Low-Intensity Laser Irradiation Test", Photomedicine and Laser Surgey, vol. 00, No. 00, pp. 1-5, year 2009.
International Application PCT/IL2011/000373 Search Report dated Sep. 27, 2011.
U.S. Appl. No. 13/669,961 office action dated Mar. 7, 2018.
U.S. Appl. No. 13/669,961 Office Action dated Jun. 5, 2018.
Vogel et al., "Optical properties of human sclera, and their consequences for transscleral laser applications.", Lasers in Surgery and Medicine , vol. 11, pp. 331-340, 1991.
International Application # PCT/IB2019/055564 search report dated Oct. 10, 2019.
Indian Patent Application # 5048/CHENP/2015 Office Action dated Dec. 31, 2019.
International Application # PCT/IB2019/059058 search report dated Feb. 16, 2020.
Das et al., "Sclera Recognition—A Survey", 2nd IAPR Asian Conference on Pattern Recognition, pp. 1-5, Naha, Japan, Nov. 5-8, 2013.
Kaya et al., "Designing a Pattern Stabilization Method Using Scleral Blood Vessels for Laser Eye Surgery", International Conference on Pattern Recognition, pp. 698-701, Istanbul, Turkey, Aug. 23-26, 2010.
EP Application # 11724805.4 Summons dated Mar. 19, 2020.

\* cited by examiner

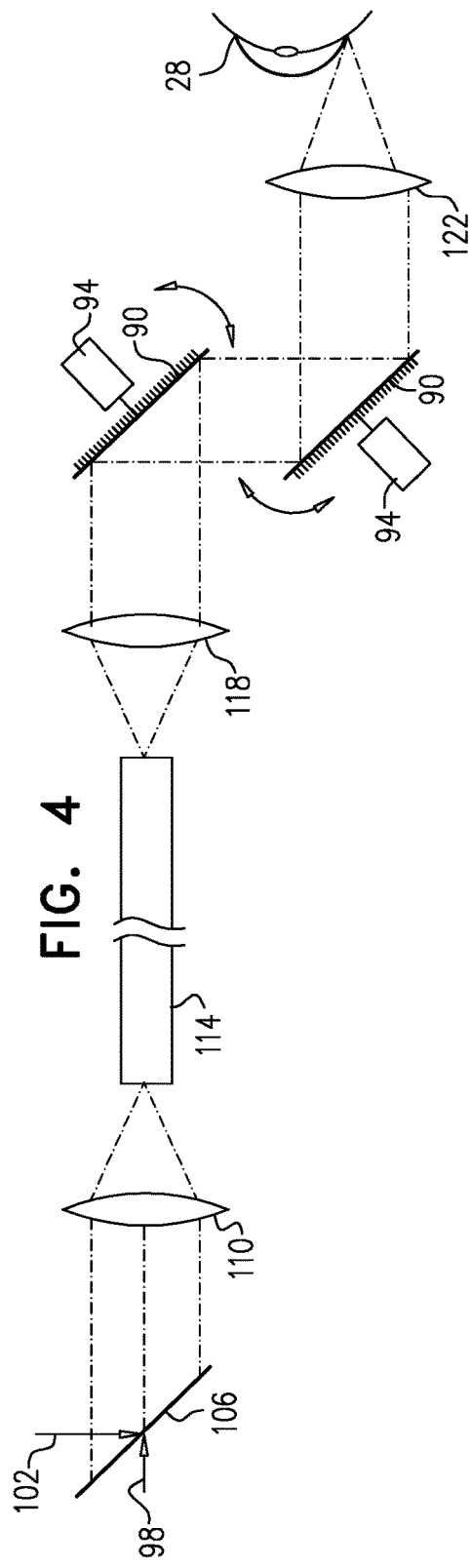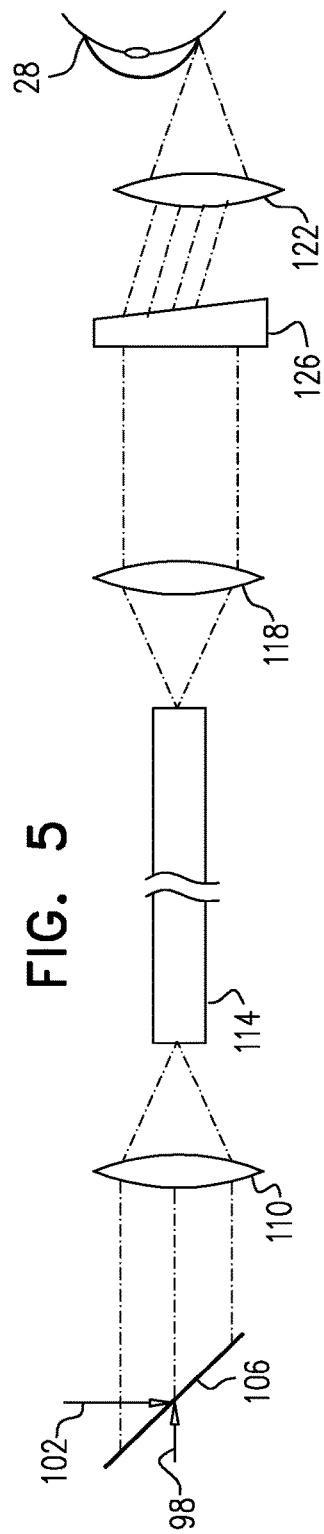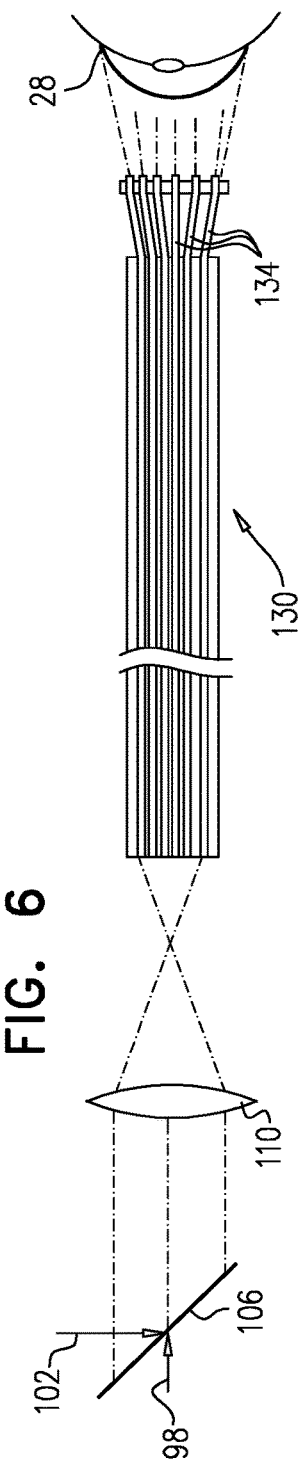

SYSTEM FOR GLAUCOMA TREATMENT

CROSS-REFERENCE TO RELATED APPLICATIONS

This application claims the benefit of U.S. Provisional Patent Application 61/769,282, filed Feb. 26, 2013, whose disclosure is incorporated herein by reference.

FIELD OF THE INVENTION

The present invention relates generally to ophthalmology, and particularly to methods and systems for eye treatment using electromagnetic energy.

BACKGROUND OF THE INVENTION

Various techniques for treating glaucoma using laser irradiation are known in the art. For example, U.S. Patent Application Publication 2003/0109907, whose disclosure is incorporated herein by reference, describes a technique for transscleral light-mediated biostimulation of the trabecular plates of a patient's eye in a treatment for glaucoma or ocular hypertension.

PCT International Publication WO/2011/00373, whose disclosure is incorporated herein by reference, describes a device for delivering electromagnetic radiation to a limbal area of an eye. PCT International Publication WO/92/16259, whose disclosure is incorporated herein by reference, describes a fiber-optic handpiece and method of use for contact cyclophotocoagulation.

U.S. Patent Application Publication 2010/0076419, whose disclosure is incorporated herein by reference, describes techniques for treating a glaucomatous eye. An amount of pulsed laser energy is delivered to the pars plana of the eye by a hand-holdable device which comprises a hand-holdable elongate member and a contact member disposed on an end of the elongate member. A contact surface of the contact member is placed in direct contact with the eye so that a reference edge of the contact member aligns with the limbus and a treatment axis defined by the elongate member is angularly offset from the optical axis of the eye.

U.S. Pat. No. 7,282,046, whose disclosure is incorporated herein by reference, describes a method and system of treating intraocular pressure. Laser light is directed to the ciliary region of the target eye. The light stimulates the ciliary region and ablates debris lodged therein. An immune response may be triggered by the stimulation of the ciliary body. Intraocular pressure is allegedly reduced by the increase in aqueous flow from the anterior chamber in the eye permitted by the resultant removal of debris blocking the uveo-scleral outflow pathway.

Laser irradiation was also suggested as a diagnostic tool for identifying hypertensive eyes at risk of glaucoma. Such techniques are described by Ivandic et al., in "Early Diagnosis of Ocular Hypertension using a Low-Intensity Laser Irradiation Test," Photomedicine and Laser Surgery, volume 27, no. 4, August, 2009, pages 571-575, which is incorporated herein by reference.

SUMMARY OF THE INVENTION

An embodiment of the present invention that is described herein provides an apparatus including a probe and a processor. The probe is positioned adjacent to an eye of a patient and is configured to irradiate a trabecular meshwork of the eye with one or more optical beams. The processor is configured to select one or more target regions of the trabecular meshwork, and to control the probe to irradiate the selected target regions with the optical beams.

In some embodiments, the processor is configured to receive a selection of one or more of the target regions from an operator. In an embodiment, the probe does not make physical contact with the eye. In a disclosed embodiment, the probe includes one of a laser diode and a NdYag laser source, which is configured to generate the optical beams.

In some embodiments, the probe includes a beam directing device that is configured to direct at least one of the optical beams toward the selected target regions. The beam directing device may include a rotating wedge prism, a scanner including one or more rotating mirrors, a bundle of optical fibers or a Diffractive Optical Element (DOE). In an example embodiment, the beam directing device includes the bundle of the optical fibers, and ends of the fibers in the bundle are tilted such that the target regions fall on an arc having a radius of curvature that depends on a distance of the ends from the eye.

In an embodiment, the processor is configured to store a record of one or more regions of the trabecular meshwork that were treated previously, and to select the target regions depending on the record. The processor may be configured to select different groups of irradiation points on a sclera around a limbus of the eye in different respective treatment sessions.

In another embodiment, the processor is configured to control the probe such that the target regions fall on a sclera around a limbus of the eye. The processor may be configured to acquire an image of the eye, to automatically recognize the target regions in the image, and to control the probe to irradiate the automatically-identified target regions. In some embodiments, the apparatus further includes an input device operated by a user, and the processor is configured to irradiate the selected target regions in response to a single activation of the input device.

In an embodiment, the probe is configured to display to the patient an object on which to focus the eye, in order to fix the eye during irradiation of the target regions. In another embodiment, the processor is configured to detect a movement of the eye, and to inhibit the irradiation in response to the detected movement. In yet another embodiment, the processor is configured to detect a movement of the eye, and to control the probe so as to track the movement of the eye with the optical beams.

The apparatus may include a protective mask, which is coupled to the eye, is opaque to the optical beams and has one or more openings surrounding the selected target regions. In an embodiment, the probe is further configured to irradiate the eye with a visible aiming beam that is aligned with the optical beams used for irradiating the target regions. The processor may be configured to automatically adjust, or direct an operator to adjust, a distance between the probe and the eye.

There is additionally provided, in accordance with an embodiment of the present invention, a method including positioning a probe adjacent to an eye of a patient so as to irradiate a trabecular meshwork of the eye with one or more optical beams. One or more target regions of the trabecular meshwork are selected using a processor. The selected target regions are irradiated with the optical beams using the probe.

The present invention will be more fully understood from the following detailed description of the embodiments thereof, taken together with the drawings in which:

BRIEF DESCRIPTION OF THE DRAWINGS

FIGS. 4-6 are block diagrams that schematically illustrate optical configurations used in a system for treating glaucoma, in accordance with embodiments of the present invention;

DETAILED DESCRIPTION OF EMBODIMENTS

Overview

Figure 1:
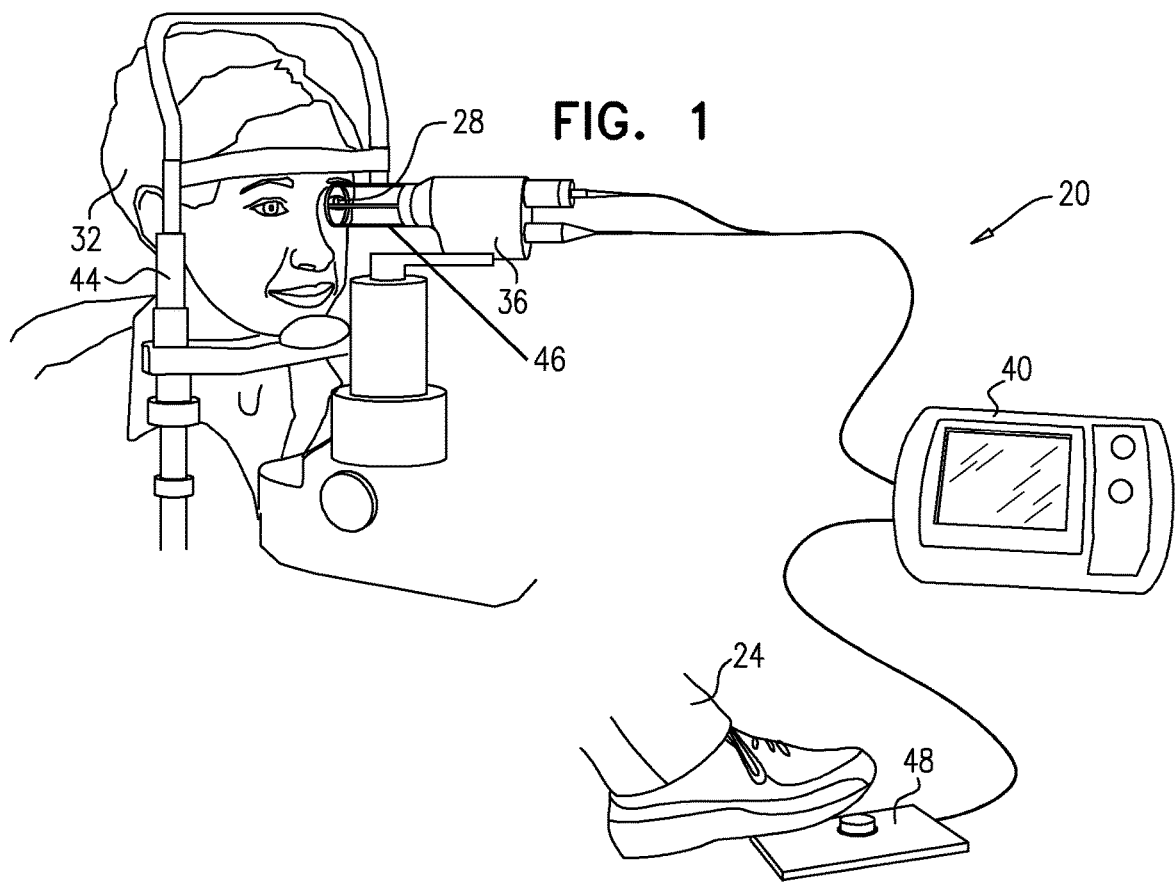
FIG. 1 is a block diagram that schematically illustrates a system for treatment of glaucoma, in accordance with an embodiment of the present invention.

Embodiments of the present invention that are described herein provide improved methods and systems for treating glaucoma. In the disclosed techniques, a probe is used for irradiating an eye of a patient with a laser beam aimed at the scleral side of the corneal limbus, i.e., the sclera around the limbus. The beam traverses the sclera and irradiates selected regions of the trabecular meshwork, thereby improving the outflow of aqueous humor via the meshwork and reducing intraocular pressure.

The laser beam is applied in a frontal direction, eliminating the need for a gonioscopic lens. Irradiation is typically performed from a distance, without requiring physical contact between the probe and the eye. Contact-less treatment of this sort is advantageous, for example, since it eliminates the need for analgesia and requires less expertise on the part of the person treating the eye. The effect of the irradiation may be non-thermal, and thus may cause little or no heating and thus damage to tissue in the vicinity of the treated area.

In the disclosed embodiments, the probe operates under control of a processor. In particular, the processor selects target regions of the trabecular meshwork that are to be irradiated, and controls the probe so as to irradiate the selected regions. As a result, laser irradiation is applied safely and with high accuracy, without requiring accuracy or expertise on the part of the person treating the eye. It is envisaged that the disclosed procedures may be performed, where permitted, by general physicians, optometrists or paramedical personnel, not only by ophthalmologists.

In some embodiments the target regions are selected automatically by the processor. In other embodiments, the processor receives the selection of the target regions from the operator. The probe typically comprises a beam directing device that is controlled by the processor and directs the laser beam toward the selected target regions. Several implementation options for the beam directing device are described herein. Typically, a complete treatment session, including irradiation of multiple spots on the sclera around the limbus, is triggered by a single push of a button.

Additional system features that are described herein include, for example, automatic identification of irradiation regions using image processing, assignment of different irradiation regions to different treatment sessions and computerized management of the multiple-session process.

The methods and systems described herein are highly effective in treating various kinds of increased intraocular pressure, such as in Open-Angle Glaucoma (OAG), Ocular Hypertension, Closed-Angle Glaucoma (Angle-Closure Glaucoma—ACG), Pigmentary Glaucoma, Pseudoexfoliative Glaucoma, Pediatric Glaucoma and Secondary Glaucoma. The automatic adjustment features enables automatic adaptation of the treatment to various eye sizes, e.g., adult vs. children eyes. Moreover, the disclosed techniques are suitable for treating Asian patients, whose eye structure is a challenge for conventional techniques.

System Description

FIG. 1 is a block diagram that schematically illustrates a system 20 for treatment of glaucoma, in accordance with an embodiment of the present invention. System 20 in this example is operated by a physician 24. The system irradiates an eye 28 of a patient 32 with one or more optical beams using techniques that are described herein, in order to reduce intraocular pressure in the eye.

Figure 7:
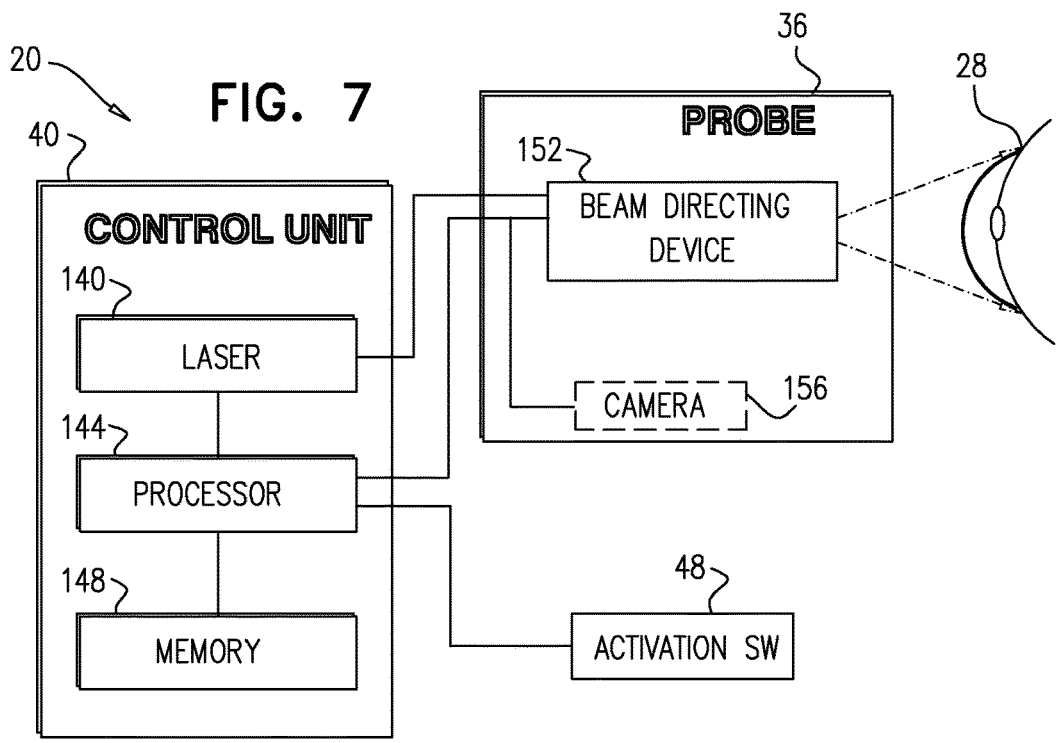
FIG. 7 is a block diagram that schematically illustrates a system for treatment of glaucoma, in accordance with an embodiment of the present invention.

In the example of FIG. 1, system 20 comprises a probe 36 and a control unit 40. Control unit 40 comprises elements such as a laser source that produces a laser aiming beam and a laser treatment beam, a processor that controls and manages the system, and other elements that are discussed in detail further below. Probe 36 and control unit 40 are connected by an optical fiber for transferring one or more laser beams from the laser in the control unit, and by electrical cabling for providing power supply and control signals. The laser typically comprises a fiber-coupled diode laser, NdYag laser source or other suitable laser source. An example block diagram of system 20, showing the elements of probe 36 and control unit 40, is shown in FIG. 7 below.

Probe 36 is positioned adjacent to the patient eye, e.g., fitted on a base or attached to a chin-rest 44 on which patient 32 places his or her head. As can be seen in the figure, a suitable fixture 46 positions the probe at a predefined distance in front of eye 28, e.g., on the order of zero to 200 mm. The laser irradiation, however, is typically performed from a distance without requiring any physical contact between the probe and the eye. Note that irradiation from a distance is not mandatory—In alternative embodiments treatment may be applied while making physical contact between probe 36 and the eye. In some embodiments probe 36 can be integrated or combined with a slit lamp. Probe 36 can also be hand-held by the treating person.

In the present example, physician 24 positions probe 36, configures control unit 40 appropriately, and then activates the laser treatment using a single activation of an activation switch 48, a push-button on unit 40, or any other suitable input device. In alternative embodiments, any other suitable system configuration can be used.

The laser beam used for treatment is referred to herein as a treatment beam. The treatment beam is typically pulsed, and may have any suitable wavelength, e.g., between Ultraviolet (UV) and far Infrared (IR) wavelengths. (The terms "treatment beam," "laser beam" and "optical beam" are sometimes used interchangeably herein.) Although the disclosed embodiments refer mainly to laser beams, the disclosed techniques are not limited to laser irradiation and may be carried out using any other suitable optical beam. The optical beams used for irradiation in the disclosed techniques may comprise non-coherent light, and may be produced by any other suitable optical source having sufficient fluence.

In an example embodiment, the wavelength of the treatment beam is chosen to be a wavelength that may be absorbed well by melanin, such as approximately 532 nm or 810±5 nm. System 20 may use treatment beams having various power levels, spot sizes and pulse durations. Example parameter values are given further below.

In some embodiments, control unit 40 produces an additional, low-power, visible laser beam, which is referred to as an aiming beam. The aiming beam is typically aligned with the treatment beam, and is used by the physician to aim the treatment beam at the desired irradiation regions, i.e., the sclera around the limbus. In an example embodiment, the aiming beam has a wavelength of 650 nm and a power level of about 1 mW. Alternatively, however, any other suitable values can be used.

Probe 36 typically receives the aiming beam and the treatment beam aligned with one another over the same optical fiber, and directs both beams using a single optical system.

Figure 2:
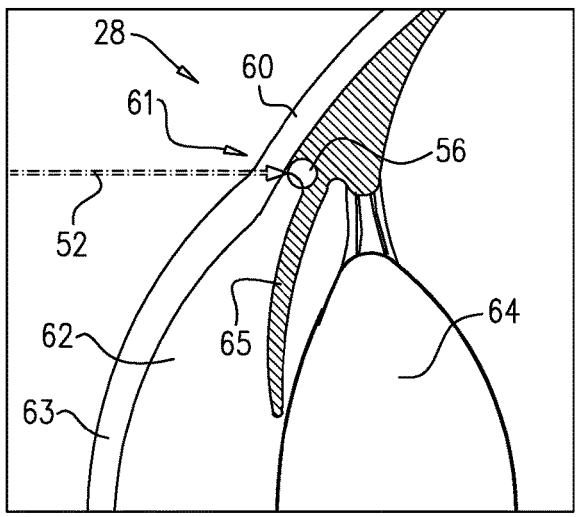
FIG. 2 is a schematic cross section of a patient eye undergoing glaucoma treatment, in accordance with an embodiment of the present invention.

FIG. 2 is a schematic cross section of eye 28 undergoing glaucoma treatment, in accordance with an embodiment of the present invention. Various elements of the eye are seen in the figure, including trabecular meshwork 56, sclera 60, cornea 63, limbus 61, iris 65, anterior chamber 62 filled with aqueous humor and lens 64. A laser beam 52 traverses the sclera and irradiates a target region in trabecular meshwork 56.

The irradiation most likely improves the permeability of the trabecular meshwork, and thus improves the outflow of aqueous humor from anterior chamber 62. As a result, intraocular pressure in the eye is reduced. The effect of the laser beam in system 20 may be non-thermal, and thus causes little or no heating and thus tissue damage in the vicinity of the treated area. Further aspects of laser treatment of this sort are addressed in PCT International Publication WO2011/00373, cited above.

Figure 3:
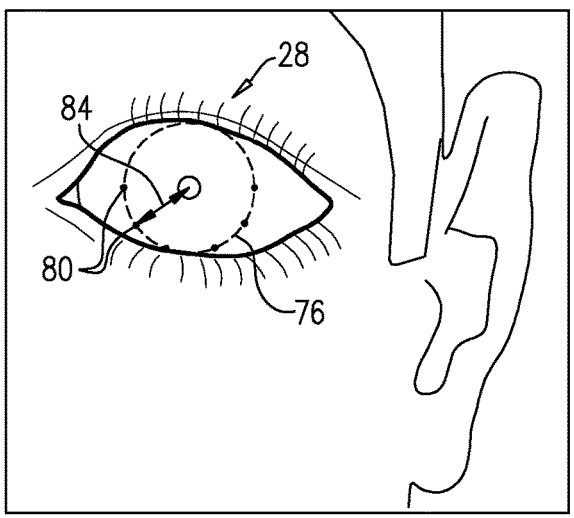
FIG. 3 is a schematic front view of a patient eye undergoing glaucoma treatment, in accordance with an embodiment of the present invention.

FIG. 3 is a schematic front view of eye 28 undergoing glaucoma treatment, in accordance with an embodiment of the present invention. The figure shows a circle 76 having a radius 84, which marks the limbus, the juncture of the cornea and sclera of eye 28. Circle 76 indicates the position of trabecular meshwork 56, which is hidden from view in this figure and is peripheral to circle 76. Irradiating any region around this circle would produce the desired therapeutic effect. The diameter of circle 76 is typically between 10-14 mm, although other values are also possible.

Figure 8:
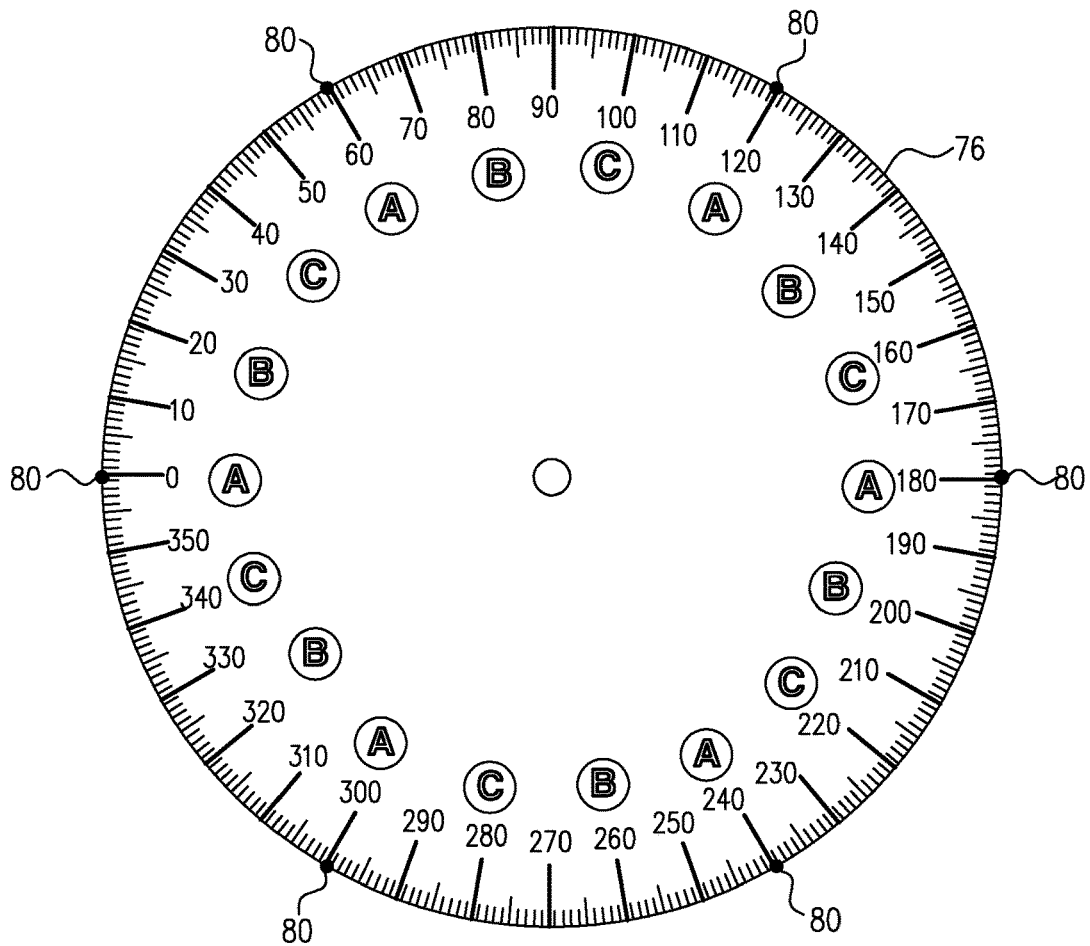
FIG. 8 is a diagram that schematically illustrates regions in a patient eye that are irradiated in multiple treatment sessions, in accordance with an embodiment of the present invention.

In some embodiments, control unit 40 selects one or more regions around circle 76, and controls probe 36 to irradiate the selected regions with one or more laser beams. The example of FIG. 3 shows a group of irradiation spots 80, which lie on the lower half of circle 76 and irradiated in response to a single activation of switch 48. A typical spot diameter is on the order of 400 μm on the surface of the sclera. In an example embodiment, probe 36 irradiates a group of six spots 80. Alternatively, unit 40 may select any other suitable number and arrangement of irradiation regions. Several examples are given below. An example of multiple different irradiation positions corresponding to multiple treatment sessions is shown in FIG. 8 below.

Example Probe Configurations

One of the main functions of probe 36 is to receive a laser beam from control unit 40, and to direct the beam to irradiate one or more regions around circle 76 that are selected by the control unit. In various embodiments, probe 36 can be implemented using different optical and mechanical configurations. In some embodiments the probe receives and directs both a treatment beam and an aiming beam.

FIG. 4 is a block diagram that schematically illustrates an optical configuration that may be used in system 20, in accordance with an embodiment of the present invention. In the present example, control unit 40 comprises a beam combiner 106 that combines a treatment beam 98 and an aiming beam 102. A lens 110 focuses and couples the two beams into an optical fiber 114 that connects the control unit with probe 36.

Upon exiting fiber 114 at probe 36, the beams are collimated by a collimating lens 118. The collimated beams are then provided to a mechanical scanner that comprises mirrors 90 mounted on respective electrical motors 94. The motors are controlled by control unit 40. Motors 94 typically rotate the mirrors around orthogonal axes, so as to direct the beam toward the desired regions of eye 28. A focusing lens 122 focuses the beam to produce the desired spot size (e.g., 400 μm).

By suitable control of motors 94, control unit 40 is able to direct the treatment and aiming beams at any desired angle. By providing suitable time-varying control signals to motors 94, control unit 40 is able to scan the laser beams in accordance with any desired spatial pattern.

In an example embodiment, unit 40 controls motors 94 to produce a pattern of multiple spots 80 around circle 76 (FIG. 3), i.e., on the sclera around the limbus. The control unit is able to control radius 84 of circle 76, the positions of spots 80 and the spacing between them around circle 76, the time spent by the beams in each spot, and/or any other suitable parameter. Moreover, the power level and pulse width of the treatment beam can also take various values.

In an example embodiment, the spot diameter is 400 μm, and radius 84 is adjustable between 5-7 mm. Example settings of the treatment beam parameters are given in the table below:

TABLE 1

Example treatment beam parameters

|  | Configuration # | | |
| --- | --- | --- | --- |
|  | I | II | III |
| Laser output power [W] | 1.2 | 5 | 2 |
| Laser pulse duration [mSec] | 300 | 72 | 180 |
| Treatment duration [Sec] | ~2 | ~0.5 | ~1 |
| Laser pulse energy [mJ] | 360 | 360 | 360 |
| Energy fluence per pulse [J/cm$^2$] | 285 | 285 | 285 |
| Laser spot diameter on sclera [μm] | 400 | 400 | 400 |

The parameters above are given purely by way of example, and any other suitable parameters can be used.

FIG. 5 is a block diagram that schematically illustrates another optical configuration that may be used in system 20, in accordance with an embodiment of the present invention. The control unit side in this configuration is similar to that of FIG. 4 above. On the probe side, after collimating lens 118, the collimated beams pass through a rotatable wedge prism 126.

Wedge prism 126 has two opposite faces that are not parallel but are tilted at a small angle relative to one another. As a result, light entering the prism along a certain axis leaves the prism along a different axis due to refraction. When the prism is rotated, the output light rotates, as well.

A lens 122 focuses the light exiting prism 126. (In alternative embodiments, lens 122 can be located before the prism.)

In this configuration, the treatment and aiming beams are rotated by wedge prism 126 so as to fall on the desired regions around circle 76 in eye 28 (FIG. 3). Radius 84 of circle 76 depends on the deviation angle applied to the beams by prism 126 and on the distance from prism 126 to eye 28. In an example embodiment, the working distance of the probe from the eye is fixed and is determined by the focal length of lens 122.

In an example embodiment, the deviation angle of the prism can be adjusted, for example, by mounting the prism in a sleeve or other fixture that permits tilting of the prism. In an alternative embodiment, the wedge prism can be moved inside its sleeve, along the optical axis, so as to change the distance between the prism and the eye.

In some embodiments, prism 126 is mounted on a suitable motor (not shown in the figure) that rotates the prism, so as to irradiate some or all of circle 76. The rotation may be performed manually or under control of control unit 40.

FIG. 6 is a block diagram that schematically illustrates yet another optical configuration that may be used in system 20, in accordance with an embodiment of the present invention. In this configuration, probe 36 comprises a bundle 130 of open-ended optical fibers 134. Any desired number of fibers 134 can be used. In an example embodiment bundle 130 comprises six fibers 134. The treatment and aiming beams are split, typically with uniform energy, among fibers 134.

The far ends of fibers 134 (on the right-hand-side of the figure) are arranged on a ring or arc having a certain radius of curvature. Thus, the probe emits multiple simultaneous beams that fall on a circle or arc in eye 36. By suitable positioning of the probe relative to the eye, the circle or arc of beams can be adjusted to coincide with circle 76 (i.e., with the circumference of cornea 63). The pattern of spots 80 of FIG. 3, for example, can be produced in this manner, one spot irradiated by each beam.

In an example embodiment, the laser parameters used with fiber bundle 130 are as follows:

TABLE 2

Example treatment beam parameters

| | |
|---|---|
| Laser output power [W] | 1.2 per spot |
| Laser pulse duration [mSec] | 300 |
| Treatment duration [Sec] | ~0.3 |
| Laser pulse energy [mJ] | 360 per spot |
| Energy fluence per pulse [J/cm$^2$] | 285 per spot |
| Laser spot diameter on sclera [μm] | 400 |

The parameters above are given purely by way of example, and any other suitable parameters can be used.

In some embodiments, fiber bundle 130 is rotatable so as to irradiate any selected sector around circle 76. The rotation may be performed manually or using a suitable motor (not shown) controlled by control unit 40.

In some embodiments, the ends of fibers 134 are tilted relative to the plane of the ring or arc on which they are arranged. In such a configuration, the radius of curvature of the circle or arc that the beams irradiate in eye 28 depends on the distance between the fiber ends and the eye. In other words, the physician may adjust the irradiation radius (radius 84 in FIG. 3) by changing the distance between probe 36 and 28.

In some embodiments, a respective lens is fitted at the end of each fiber 134 in order to prevent divergence of the beams leaving the fibers. Various small-size lens types can be used for this purpose, such as micro-lenses or Gradient Index (GRIN) lenses.

Further alternatively, probe 36 may comprise any other suitable type of beam directing device that directs the input laser beam or beams toward the desired irradiation regions around circle 76. For example, the probe may comprise a Diffractive Optical Element (DOE), as described in PCT International Publication WO/2011/00373, cited above.

Additional System Features, Embodiments and Variations

FIG. 7 is a block diagram that schematically illustrates system 20, in accordance with an embodiment of the present invention. The figure shows an example configuration of probe 36 and control unit 40.

Control unit 40 comprises a laser source 140 that produces the treatment beam and optionally the aiming beam. Laser source 140 may comprise, for example, a fiber-coupled diode laser or NdYag laser source. A processor 144 controls the various system elements and carries out the methods disclosed herein. Among other tasks, processor 144 selects the desired irradiation regions (e.g., spots 80 in FIG. 3) and controls probe 36 to irradiate them. Processor 144 stores data in a memory 148.

Probe 36 comprises a beam directing device 152 that receives the laser beam from laser source 140 and directs the beam toward the irradiation regions selected by processor 144. As explained above, device 152 may be implemented in various configurations, such as using a scanner (FIG. 4), wedge prism (FIG. 5) fiber bundle (FIG. 6) or DOE or other suitable type of beam directing device.

In some embodiments, probe 36 comprises a camera 156 that acquires an image of eye 28 and transfers the image to processor 144. The processor automatically identifies the sclera around the limbus in the image, using any suitable image processing algorithm. Using the identified cornea circumference, the processor determines the desired radius of circle 76 and controls device 152 accordingly. This technique enables system 20 to match the irradiation regions automatically to various eye sizes and various probe-eye distances.

In an example implementation, processor 144 directs the irradiation beams automatically to the target regions by identifying in the image (1) the cornea boundary (the sclera around the limbus), and (2) the circle formed by the aiming beam, and then iteratively adjusting the irradiation radius until the two coincide.

Camera 156 may also be used for general-purpose filming and recording of the procedure.

In alternative embodiments, the irradiation radius (the radius of curvature of the circle on which spots 80 lie) is adjusted manually by physician 24 using control unit 40. Typically, the physician views the arch, circle or other shape formed by the aiming beam on the eye surface, and enters commands that instruct processor 144 to adjust the shape. The processor controls device 152 accordingly.

For example, control unit may have "up/down/left/right" controls or a joystick for moving the arch or circle and "increase radius/decrease radius" controls that change the radius of the circle. The control unit may also have controls that select a desired sector of the circle to be irradiated, the number or density of spots 80, or any other suitable parameter. In some embodiments, the irradiated shape may not necessarily be part of a circle and may comprise, for example, an ellipse or other suitable shape. These adjustments are typically made solely by controlling beam directing device 152, without physically moving probe 36 relative to the eye.

In some embodiments, processor 144 estimates the distance between probe 36 and the patient eye. In some embodiments, the processor also adjusts the distance automatically. In alternative embodiments, processor 144 produces an indication that enables the physician to manually adjust the probe-eye distance.

In one example embodiment, processor 144 analyzes the images of the eye that are acquired by camera 156 at various probe-eye distances. The processor identifies the imprint of the aiming beam on the eye, and attempts to find the distance in which the aiming beam imprint has the smallest spot size. In other embodiments, processor 144 may perform a similar process using the imprint of the treatment beam, without a need for an aiming beam, provided that the treatment beam is visible to camera 156.

In an example embodiment, processor 144 identifies the ring-shaped imprint of the aiming or treatment beam in the images, and adjusts (or directs the physician to adjust) the probe-eye distance so as to converge to the thinnest ring imprint. Alternatively, processor 144 may use any other suitable distance estimation and/or adjustment method.

In some embodiments, processor 144 defines multiple different groups of irradiation spots 80, each group to be used in a different treatment session. Experience has shown that the effectiveness of laser irradiation of the trabecular meshwork diminishes over time. One possible solution is to perform several treatment sessions on the same eye, e.g., several years apart, and irradiate a different region of the trabecular meshwork in each session.

In some embodiments, processor 144 manages this multi-session treatment automatically. For example, the processor may predefine multiple different groups of spots 80, one group pre-assigned to session A, another group pre-assigned to session B, and so on. In each session, the physician enters the session number to control unit 40. Processor 144 then controls beam directing device 152 to irradiate the spots belonging to the corresponding group. Alternatively, processor 144 may record the number of sessions performed on each patient, e.g., per patient ID. Using these management techniques, system 20 is able to apply the appropriate irradiation in each session and eliminate human errors. The definitions of spot groups, session numbers per patient ID, and/or any other suitable information, is typically stored by processor 144 in memory 148.

FIG. 8 is a diagram that schematically illustrates regions in a patient eye that are irradiated in multiple treatment sessions of a given treatment protocol, in accordance with an example embodiment of the present invention. The figure shows circle 76 that coincides with limbus 61, i.e., the perimeter of cornea 63. Three groups of irradiation spots are predefined for use in three respective treatment sessions denoted A, B and C.

Spots 80 relating to session A are marked in the figure, at angles {0°, 60°, 120°, 180°, 240° and 300°} on circle 76. The spots for session B are defined at angles {20°, 80°, 140°, 200°, 260° and 320°}, and the spots for session C are defined at angles {40°, 100°, 160°, 220°, 280° and 340°}.

The treatment protocol shown in FIG. 8 is chosen purely by way of example. In alternative embodiments, any other suitable protocol can be used, e.g., protocols with different numbers of sessions and/or protocol with different definitions of irradiation regions per session. For example, the different groups of spots may all lie on a partial sector of circle 76, e.g., on the bottom half or top half of the circle.

It is typically important that the patient eye will be fixed in space during the laser irradiation. Movement of the eye will cause irradiation of the wrong regions, and may have safety implications. Reducing eye movement is one of the reasons for defining the irradiation spots on the top or bottom half of circle 76. In these embodiments, the patient is instructed to look up (in case of irradiating the bottom half of the circle) or down (in case of irradiating the top half). In this position the possible movement of the eye is reduced considerably.

In some embodiments, in order to reduce eye movement, probe 36 projects an object for the patient to focus on during the treatment. The object may comprise, for example, an icon or light point at a fixed location. This mechanism helps to fix the patient's eye during the treatment.

In some embodiments, system 20 comprises a safety mechanism that inhibits the laser irradiation automatically upon detecting that the patient eye has moved from its intended position by more than a tolerable amount. For example, when using camera 156 and the associated image processing scheme described above, processor 144 can take images of the eye periodically during the treatment session, and verify in the images whether the eye is still in its intended position relative to the irradiation pattern.

In one embodiment, if the images indicate an intolerable movement of the eye, processor 144 inhibits the laser irradiation. In another embodiment, if the images indicate an intolerable movement of the eye, processor 144 instructs device 152 to move the treatment beam so as to track to eye movement.

The configurations of system 20, probe 36 and control unit 40 shown in FIGS. 1 and 4-7 are example configurations that are chosen purely for the sake of conceptual clarity. In alternative embodiments, any other suitable configuration can be used. Certain elements may be implemented using hardware/firmware. Alternatively, some elements may be implemented in software or using a combination of hardware/firmware and software elements.

In some embodiments, certain functions of control unit 40, such as some or all of the functions of processor 144, may be implemented using a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

In some embodiments, the safety of the disclosed procedure is enhanced by placing a protective mask on eye 28. The mask is opaque to the wavelength used for irradiation. The mask is typically shaped and placed similarly to a contact lens. In one embodiment, the mask covers the entire cornea plus part of the surrounding sclera (e.g., a 5 mm additional band of the sclera). The mask has a number of openings surrounding the desired irradiation target regions. The mask may be fabricated from any suitable material and may comprise any suitable number of openings of any suitable shapes.

In some embodiments, although not necessarily, the mask is disposable. Such a mask enhances the safety of the procedure because it prevents irradiation outside the desired regions from reaching the eye. The use of a protective mask may, for example, promote the use of the disclosed techniques by non-ophthalmologists such as general physicians, optometrists or paramedical personnel.

In various embodiments, system 20 may comprise means for billing a usage-dependent fee for using the system. Any suitable business model, usage tracking mechanism and billing mechanism can be used for this purpose. For example, processor 144 may be pre-charged with a certain usage credit, and then decrement the remaining credit with every activation. The usage credit may be expressed in terms of a number of activations, in terms of irradiation energy (e.g., Joules), in terms of usage subscription time (e.g., months) or in any other suitable way. Re-charging of usage credit can be performed in any suitable manner, such as over the Internet, phone or cellular network, or using a removable memory module (e.g., USB plug) that can be charged with credit or activation code.

Experimental Results

The effectiveness of the disclosed techniques was evaluated experimentally on human patients. The purpose of the test was to evaluate whether direct application of Selective Laser Trabeculoplasty (SLT) irradiation to the perilimbal area is effective in reducing Intraocular Pressure (IOP), eliminating the need for gonioscopy during the procedure.

A randomized, masked, controlled trial was performed on OAG and Pseudoexfoliative Glaucoma patients. The control group underwent conventional SLT, delivering 100 laser spots through a gonioscopy lens to 360 degrees of the trabecular meshwork (TM). The trial group underwent irradiation by the same laser at the same irradiation parameters, but instead of delivering the energy through a gonioscopy lens, a similar number of applications were administered all around the limbus on the sclera overlying the TM. IOP was measured and side effects evaluated 1, 7, 30, 60, 180 and 360 days after treatment.

In the trial group (n=13), IOP decreased from an average of 20.0 mmHg before treatment to 16.8 at 1 week (n=13), 16.1 mmHg at 1 month (n=12), 15.8 mmHg at 2 months (n=10), and 14.2 mmHg at 6 months (n=5). The corresponding numbers for the control group (n=14), were 21.5 mmHg, 16.8 mmHg (n=14), 14.8 mmHg (n=13), 14.4 mmHg (n=10) and 15.4 mmHg (n=7), respectively.

There was no statistical difference between the two groups in IOP reduction (P=0.319, 0.776, 0.980, 0.415, 0.391, 0.917) for the IOP on recruitment, 1, 7, 30, 60, 180 and 360 days post SLT respectively, [Mann Whitney]. There was no statistically-significant difference between the groups [P=0.704, Fisher]. Success was defined as >20% IOP reduction. There was no statistically-significant differences in success rates 2 and 6 months after treatment [P=0.582, 0.558, Fisher]. 1 and 7 patients showed mild transient inflammatory response post treatment in the trial and control groups, respectively with significantly less superficial punctate keratitis recorded on the treatment day in the study group (p<0.01).

Another SLT experiment was performed on a trial group and a control group of 15 open-angle and pseudoexfoliation glaucoma patients each. The control group underwent conventional SLT, delivering 100 laser spots through a gonioscope for 360 degrees of the TM. The trial group underwent irradiation by the same laser (NdYag, 532 nm) with the same parameters, but applications were administered at the perilimbal area overlying the TM. IOP was measured and side effects evaluated 1, 7, 30, 60 and 180 days after treatment.

The mean (±SD) pre-treatment IOP was 20.21±3.19 mmHg and 21.14±2.98 mmHg in the trial and control groups, respectively (p=). The mean (±SD) post-treatment IOP dropped to 15.50±3.77 mmHg and 15.00±4.08 mmHg in the trial and control groups, respectively (p=0.744, 0.96595% CI 0.789/1.182) at 6 months visit [Mann Whitney]. IOP reduction was similar in both groups throughout the study, with an average IOP reduction of 23.4% and 27.1% after 6 months, in the trial and control groups, respectively (p=0.528, OR 0.982, 95% CI0.932/1.036). Success (defined as having reached a decrease of ≥15% in IOP from baseline by the time of 6 months visit with no additional hypotensive medications, laser, or glaucoma surgery) was attained in 12 (85.7%) and 9 (64.3%) patients in the study and control groups, respectively. (p=x), [Fisher]. All documented complications were mild and transient. Complications rate was significantly higher in the control group (p<0.0001, OR 6.881, 95% CI 1.676/28.248), specifically anterior chamber inflammation and superficial punctate keratitis, which were significantly higher in the control group (p=0.006).

Conclusions: The effectiveness of trans-scleral SLT depends on the laser energy penetrating a few millimeters into tissue to impact the TM. Laser coherency, lost in tissue transmission, is not required. It seems that SLT applied directly to the perilimbal sclera is as efficacious as the conventional gonioscopy-assisted procedure, and that the use of a gonioscopy lens is not necessary. As the long-term IOP reduction of SLT can be discerned within a few days after treatment, it is likely that the technique will be as effective as the conventional one. If so, the disclosed techniques will simplify and shorten the SLT procedure considerably and eliminate the corneal and gonioscopy-induced side effects of SLT.

Yet another experiment was performed on five patients, using a probe that applied laser irradiation to the limbus on the sclera overlying the TM. The probe in this experiment was in physical contact with the eye, but simulated similar irradiation parameters to those disclosed herein (i.e., six irradiation spots, similar energy level). All patients exhibited a considerable decrease in IOP, between 20-38%.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
   a probe, which is adapted to be positioned adjacent to an eye of a patient and is configured to irradiate a trabecular meshwork of the eye with one or more optical beams;
   a fixture, adapted to position the probe at a predefined distance in front of the eye such that the probe does not make physical contact with the eye, wherein the probe comprises a beam directing device that is controllable to direct at least one of the optical beams, through the fixture, toward the eye; and
   a processor, which is configured to:
     receive an acquired image of the eye;
     identify in the image a limbus of the eye;
     define, on a surface of the eye in a vicinity of the limbus, based on identification of the limbus in the image, a shape having a radius, a size of the radius selected such that any one or more irradiation regions on the shape, when irradiated with the one or more optical beams, cause the one or more optical beams to hit respective target regions of the trabecular meshwork that are hidden from view; and control the beam directing device in the probe, based on the image, to irradiate selected irradiation regions on the shape defined on the surface of the eye in the vicinity of the limbus, thereby irradiating the hidden target regions of the trabecular meshwork with the one or more optical beams.

2. The apparatus according to claim 1, wherein the processor is configured to receive a selection of one or more of the target regions from an operator.

3. The apparatus according to claim 1, wherein the probe comprises a laser source selected from a group consisting of a laser diode, a NdYag laser source and a 532 nm laser source, which is configured to generate the optical beams.

4. The apparatus according to claim 1, wherein the beam directing device is selected from a group consisting of:
   a rotating wedge prism;
   a scanner comprising one or more rotating mirrors;
   a bundle of optical fibers; and
   a Diffractive Optical Element (DOE).

5. The apparatus according to claim 4, wherein the beam directing device comprises the bundle of the optical fibers, and wherein ends of the fibers in the bundle are tilted such that the target regions fall on an arc having a radius of curvature that depends on a distance of the ends from the eye.

6. The apparatus according to claim 1, wherein the processor is configured to store a record of one or more regions of the trabecular meshwork that were treated previously, and to select the target regions depending on the record.

7. The apparatus according to claim 6, wherein the processor is configured to select different groups of the irradiation regions in the vicinity of the limbus of the eye in different respective treatment sessions.

8. The apparatus according to claim 1, wherein the processor is configured to control the probe such that the target regions fall on a sclera around the limbus of the eye.

9. The apparatus according to claim 1, and comprising an input device operated by a user, wherein the processor is configured to irradiate the selected target regions in response to a single activation of the input device.

10. The apparatus according to claim 1, wherein the probe is configured to display to the patient an object on which to focus the eye, in order to fix the eye during irradiation of the target regions.

11. The apparatus according to claim 1, wherein the processor is configured to detect a movement of the eye, and to inhibit the irradiation in response to the detected movement.

12. The apparatus according to claim 1, wherein the processor is configured to detect a movement of the eye, and to control the probe so as to track the movement of the eye with the optical beams.

13. The apparatus according to claim 1, and comprising a protective mask, which is adapted to be coupled to the eye, is opaque to the optical beams and has one or more openings surrounding the selected target regions.

14. The apparatus according to claim 1, wherein the probe is further configured to irradiate the eye with a visible aiming beam that is aligned with the optical beams used for irradiating the target regions.

15. The apparatus according to claim 1, wherein the processor is configured to automatically adjust, or direct an operator to adjust, a distance between the probe and the eye.

16. The apparatus according to claim 1, wherein the shape comprises a circle or an ellipse having the radius.

17. A method, comprising:
   positioning a probe adjacent to an eye of a patient, using a fixture that positions the probe at a predefined distance in front of the eye, such that the probe does not make physical contact with the eye, so as to irradiate a trabecular meshwork of the eye with one or more optical beams, wherein the probe comprises a beam directing device that is controllable to direct at least one of the optical beams, through the fixture, toward the eye; and
   using a processor:
      receiving an acquired image of the eye;
      identifying in the image a limbus of the eye;
      defining, on a surface of the eye in a vicinity of the limbus, based on identification of the limbus in the image, a shape having a radius, a size of the radius selected such that any one or more irradiation regions on the shape, when irradiated with the one or more optical beams, cause the one or more optical beams to hit respective target regions of the trabecular meshwork that are hidden from view; and
      controlling the beam directing device in the probe, based on the image, to irradiate selected irradiation regions on the shape defined on the surface of the eye in the vicinity of the limbus, thereby irradiating the hidden target regions of the trabecular meshwork with the one or more optical beams.

18. The method according to claim 17, and comprising receiving a selection of one or more of the target regions from an operator.

19. The method according to claim 17, wherein irradiating the vicinity of the limbus comprises treating glaucoma in the eye.

20. The method according to claim 17, wherein irradiating the vicinity of the limbus comprises reducing intraocular pressure in the eye.

21. The method according to claim 17, and comprising generating the optical beams using a laser source selected from a group consisting of a laser diode, a NdYag laser source, and a 532 nm laser source.

22. The method according to claim 17, wherein the beam directing device is selected from a group consisting of:
   a rotating wedge prism;
   a scanner comprising one or more rotating mirrors;
   a bundle of optical fibers; and
   a Diffractive Optical Element (DOE).

23. The method according to claim 22, wherein the beam directing device comprises the bundle of the optical fibers, and wherein ends of the fibers in the bundle are tilted such that the target regions fall on an arc having a radius of curvature that depends on a distance of the ends from the eye.

24. The method according to claim 17, and comprising storing a record of one or more regions of the trabecular meshwork that were treated previously, and selecting the target regions depending on the record.

25. The method according to claim 24, and comprising selecting different groups of the irradiation regions in the vicinity of the limbus of the eye in different respective treatment sessions.

26. The method according to claim 17, wherein irradiating the vicinity of the limbus comprises causing the target regions to fall on a sclera around the limbus of the eye.

27. The method according to claim 17, wherein irradiating the vicinity of the limbus comprises irradiating the vicinity of the limbus in response to a single activation of an input device operated by a user.

28. The method according to claim 17, and comprising displaying to the patient an object on which to focus the eye, in order to fix the eye during irradiation of the target regions.

29. The method according to claim 17, and comprising detecting a movement of the eye, and inhibiting the irradiation in response to the detected movement.

30. The method according to claim 17, and comprising detecting a movement of the eye, and tracking the movement of the eye with the optical beams.

31. The method according to claim 17, and comprising coupling to the eye a protective mask that is opaque to the optical beams and has one or more openings surrounding the selected target regions.

32. The method according to claim 17, and comprising irradiating the eye with a visible aiming beam that is aligned with the optical beams used for irradiating the target regions.

33. The method according to claim 17, and comprising automatically adjusting, or directing an operator to adjust, a distance between the probe and the eye.

34. The method according to claim 17, wherein defining the shape comprises defining a circle or an ellipse having the radius.

\* \* \* \* \*